(12) United States Patent
Tanaka et al.

(10) Patent No.: US 8,058,261 B2
(45) Date of Patent: Nov. 15, 2011

(54) 3'-ETHYNYLCYTIDINE DERIVATIVE

(75) Inventors: Motoaki Tanaka, Chiyoda-ku (JP); Masakazu Fukushima, Tokushima (JP)

(73) Assignees: Taiho Pharmaceutical Co., Ltd., Tokyo (JP); Takuma Sasaki, Nagoya-shi (JP); Akira Matsuda, Sapporo-shi (JP)

( * ) Notice: Subject to any disclaimer, the term of this patent is extended or adjusted under 35 U.S.C. 154(b) by 349 days.

(21) Appl. No.: 12/375,077

(22) PCT Filed: Jul. 23, 2007

(86) PCT No.: PCT/JP2007/000787
§ 371 (c)(1),
(2), (4) Date: Jan. 26, 2009

(87) PCT Pub. No.: WO2008/012945
PCT Pub. Date: Jan. 31, 2008

(65) Prior Publication Data
US 2009/0306008 A1 Dec. 10, 2009

(30) Foreign Application Priority Data
Jul. 24, 2006 (JP) ................................ 2006-200587

(51) Int. Cl.
*A01N 43/04* (2006.01)
*A61K 31/70* (2006.01)

(52) U.S. Cl. ........... 514/49; 514/43; 536/28.1; 536/28.4

(58) Field of Classification Search ........................ None
See application file for complete search history.

(56) References Cited

U.S. PATENT DOCUMENTS

| 5,061,793 A | 10/1991 | Grindey et al. |
| 5,464,826 A | 11/1995 | Grindey et al. |
| 5,763,418 A | 6/1998 | Matsuda et al. |

FOREIGN PATENT DOCUMENTS

| JP | 61-148193 | 7/1986 |
| JP | 10 298194 | 11/1998 |
| WO | 96 18636 | 6/1996 |

OTHER PUBLICATIONS

Nowak et al. J. Org. Chem. (2005), vol. 70, pp. 7455-7458.*
Robins et al. Can. J. Chem. (1981), vol. 59, pp. 2608-2611.*
Hattori, H. et al., "Nucleosides and Nucleotides. 175. Structural Requirements of the Sugar Moiety for the Antitumor Activities of New Nucleoside Antimetabolites, 1-(3-C-Ethynyl-β-D-ribo-pentofuranosyl)cytosine and-uracil[1]", Journal of Medicinal Chemistry, vol. 41, No. 15, pp. 2892-2902, (1998).
Hattori, H. et al. "Nucleosides and Nucleotides. 158. 1-(3-C-Ethynyl-β- D-ribo pentofuranosyl)-cytosine, 1-(3-C-Ethynyl-β-D-ribo-pentofuranosyl)uracil, and Their Nucleobase Analogues as New Potential Multifunctional Antitumor Nucleosides with a Broad Spectrum of Activity[1]", Journal of Medicinal Chemistry, vol. 39, No. 25, pp. 5005-5011, (1996).
Nomura, M. et al., "Nucleosides and nucleotides. Part 212: Practical large-scale synthesis of 1-(3-C-ethynyl-β-D-ribo-pentofuranosyl)cytosine (ECyd), a potent antitumor nucleoside. Isobutyryloxy group as an efficient anomeric leaving group in the Vorbrueggen glycosylation reaction", Tetrahedron, vol. 58, No. 7, pp. 1279-1288, (2002).
John S. Evans, et al., "Antitumor Activity of 1-β-D-Arabinofuranosylcytosine Hydrochloride", Proc. Soc. Exp. Bio. Med., vol. 106, 1961, pp. 350-353.
Akio Hoshi, et al., "Antitumor Activity of 1-Hexylcarbamoyl-5-Fluorouracil in a Variety of Experimental Tumors", Gann, vol. 67, No. 5, Oct. 1976, pp. 725-731.
Satoshi Tabata, et al., "Antitumor effect of a novel multifunctional antitumor nucleoside, 3'-ethynylcytidine, on human cancers", Oncology Reports, vol. 3, 1996, pp. 1029-1034.
Motohiro Tanaka, et al., Cancer & Chemotherapy, vol. 24-4, 1997, pp. 476-482.
Peter S. Ludwig, et al., "A New Laboratory Scale Synthesis for the Anticancer Drug 3'-C-Ethynylcytidine", Synthesis, No. 16, 2002, pp. 2387-2392.

* cited by examiner

*Primary Examiner* — Patrick Lewis
(74) *Attorney, Agent, or Firm* — Oblon, Spivak, McClelland, Maier & Neustadt, L.L.P.

(57) ABSTRACT

To provide a compound which exhibits excellent anti-tumor activity and excellent oral absorption and which is a useful anti-tumor drug.

The invention provides a 3'-ethynylcytidine derivative represented by formula (1):

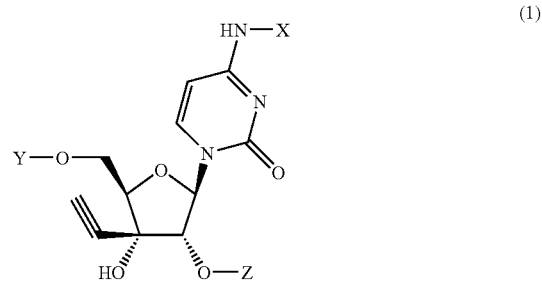

(wherein X represents a (substituted) alkylcarbonyl group, a (substituted) alkoxycarbonyl group, or a hydrogen atom; one of Y and Z represents a hydrogen atom or a group represented by $(R^1)(R^2)(R^3)Si$— and the other represents a group represented by $(R^4)(R^5)(R^6)Si$—; and $R^1$, $R^2$, $R^3$, $R^4$, $R^5$, and $R^6$ each represent a (substituted) alkyl group, a (substituted) cyclic alkyl group, or a (substituted) aryl group) or a salt thereof.

15 Claims, No Drawings

3'-ETHYNYLCYTIDINE DERIVATIVE

CROSS-REFERENCE TO RELATED APPLICATIONS

This application is a 371 of PCT/JP07/00787 filed Jul. 23, 2007 and claims the benefit of JP 2006-200587 filed Jul. 24, 2006.

TECHNICAL FIELD

The present invention relates to 3'-ethynylcytidine derivatives possessing excellent anti-tumor effects.

BACKGROUND ART

Cancer, which is characterized by anomalous cell proliferation, still continues to be an intractable disease, so it is keenly needed that a therapeutic agent effective for its treatment be developed any time soon. Based on the knowledge that a biosynthesis of nucleic acid is essential for cell proliferation, many researches have energetically been conducted in order to obtain a metabolism antagonist capable of inhibiting nucleic-acid metabolism. So far, cytidine-based metabolism antagonists have been developed and are now used clinically for cancer treatments. For example, cytarabine (Non-Patent Document 1), ancitabine (Non-Patent Document 2), and gemcitabine (Patent Document 1), which exhibit anti-tumor activities through the inhibition of DNA synthesis, can be mentioned as such antagonists. Meanwhile, 3'-ethynylpyrimidine nucleoside containing 3'-ethynylcytidine (ECyd), which was developed by Matsuda et al., is known as a nucleic acid metabolism antagonist capable of inhibiting RNA synthesis (Patent Document 2, and Non-Patent Documents 3 and 4).

ECyd is known to possess an excellent anti-tumor effect more greatly than any of fluoropyrimidine-based drugs, against 5 strains of gastric cancer, 3 strains of colon cancer, 2 strains of pancreatic cancer, 1 strain of each of esophageal cancer, bile duct cancer, lung cancer, breast cancer and renal cancer, as confirmed by a method comprising an intravenous administration (0.25 mg/kg for ten continuous days) to nude mice subcutaneously transplanted with human tumor cells (Non-Patent Documents 5 and 6).

However, such intravenous administration drugs have many problems such as mental and physical pains of cancer patients and the higher medical cost attributable to outpatient treatment. If it is possible to substitute a oral drug for such intravenous administration drugs, and to thereby bring in nearly the same therapeutic effect, the quality of life (QOL) of patients is expected to improve dramatically. Nonetheless, the oral administration of ECyd is much less likely to exhibit such a high anti-tumor effect than the intravenous administration. Therefore, there has been a keen demand for the development of an oral drug having an anti-tumor activity equivalent to that obtained by the intravenous administration of ECyd.

[Patent Document 1] Japanese Patent Publication (kokoku) No. 37394/1994

[Patent Document 2] JP-B-3142874

[Non-Patent Document 1] Evance, J. S. et al. Proc. Soc. Exp. Bio. Med., 106, 350 (1961)

[Non-Patent Document 2] Hoshi, A. et al. Gann, 67, 725 (1972)

[Non-Patent Document 3] Hattori, H. et al. J. Med. Chem. 39, 5005-5011 (1996)

[Non-Patent Document 4] Hattori, H. et al. J. Med. Chem., 41, 2892-2902 (1998)

[Non-Patent Document 5] Oncology Report Vol. 3, 1029 to 1034, 1996

[Non-Patent Document 6] Motohiro Tanaka et al., Cancer & Chemotherapy Vol. 24-4, pp. 476 to 482, 1997

[Non-Patent Document 7] Ludwig, P. S. et al. Synthesis (2002) 2387-2392

DISCLOSURE OF THE INVENTION

Problems to be Solved by the Invention

In view of the forgoing, an object of the present invention is to provide an ECyd derivative exhibiting an anti-tumor effect higher than that of ECyd when orally administered.

Means for Solving the Problems

In an attempt to attain the aforementioned object, the present inventors have conducted extensive studies, and have found that a 3'-ethynylcytidine derivative represented by the following formula (1) or a salt thereof exhibits excellent anti-tumor activity when orally administered. The present invention has been accomplished on the basis of this finding.

Accordingly, the present invention provides a 3'-ethynylcytidine derivative represented by formula (1):

[F1]

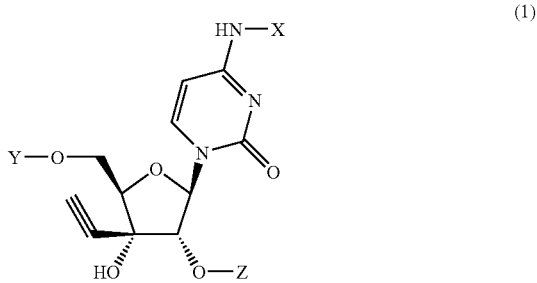

(1)

(wherein X represents a hydrogen atom, an alkylcarbonyl group of which alkyl moiety is a C1-C6 linear or branched alkyl group which may have a substituent, or an alkoxycarbonyl group of which alkoxy moiety is a C1-C6 linear or branched alkoxy group which may have a substituent; one of Y and Z represents a hydrogen atom or a group $(R^1)(R^2)(R^3)$Si— and the other represents a group $(R^4)(R^5)(R^6)$Si—; and $R^1$, $R^2$, $R^3$, $R^4$, $R^5$, and $R^6$, which may be identical to or different from one another, each represent a C1-C10 linear or branched alkyl group which may have a substituent, a C3-C6 cycloalkyl group which may have a substituent, or a C6-C14 aryl group which may have a substituent) or a salt thereof.

The present invention also provides a pharmaceutical composition containing a compound represented by formula (1) or a salt thereof and a pharmaceutical carrier.

The present invention also provides an anti-tumor drug containing a compound represented by formula (1) or a salt thereof and a pharmaceutical carrier.

The present invention also provides a oral anti-tumor drug containing a compound represented by formula (1) or a salt thereof and a pharmaceutical carrier.

The present invention also provides use of a compound represented by formula (1) or a salt thereof for producing a drug, particularly an anti-tumor drug.

The present invention also provides a method for treatment of tumor, characterized in that the method comprises administering a compound represented by formula (1) or a salt thereof in an effective amount to a subject in need thereof.

Effects of the Invention

The 3'-ethynylcytidine derivative or a salt thereof of the present invention is a useful anti-tumor drug which exhibits excellent anti-tumor activity and excellent oral absorption.

BEST MODES FOR CARRYING OUT THE INVENTION

The 3'-ethynylcytidine derivative or a salt thereof of the present invention is a compound represented by formula (1), the compound having a chemical structure in which a silyl group has been introduced to the 2'- and/or 5'-position hydroxyl group.

One known compound of the 3'-ethynylcytidine derivatives having a silyl group at 2'- or 5'-position is 4-N-benzoyl-2'-O-(tert-butyldimethylsilyl)-3'-C-trimethylsilylethynylcytidine (Non-Patent Document 7). However, this compound structurally differs from the 3'-ethynylcytidine derivative of the present invention in that the known compound has a trimethylsilyl group as a 3'-position substituent on the ethynyl group and has a benzoyl group as a 4-N-position substituent. Furthermore, the known compound is disclosed merely as a synthesis intermediate, and no anti-tumor activity of the compound is reported.

Examples of the "C1-C6 linear or branched alkyl group" of the "alkylcarbonyl group of which alkyl moiety is a C1-C6 linear or branched alkyl group which may have a substituent(s)" represented by X in formula (1) include methyl, ethyl, n-propyl, isopropyl, n-butyl, isobutyl, tert-butyl, n-pentyl, and n-hexyl. Of these, C1-C6 linear alkyl groups are preferred, with methyl and n-hexyl being more preferred. Examples of the "substituent" of the "alkylcarbonyl group of which alkyl moiety is a C1-C6 linear or branched alkyl group which may have a substituent(s)" represented by X in formula (1) include an amino group of which one or two hydrogen atoms are substituted by a C1-C6 linear or branched alkyl group; e.g., methylamino, dimethylamino, and diethylamino. Of these, an amino group of which two hydrogen atoms are substituted by a C1-C6 linear or branched alkyl group is preferred, with dimethylamino being more preferred.

Examples of the "C1-C6 linear or branched alkoxy group" of the "alkoxycarbonyl group of which alkoxy moiety is a C1-C6 linear or branched alkoxy group which may have a substituent(s)" represented by X in formula (1) include methoxy, ethoxy, n-propoxy, isopropoxy, n-butoxy, isobutoxy, tert-butoxy, n-pentyloxy, and n-hexyloxy. Of these, C1-C4 linear or branched alkoxy groups are preferred, with tert-butoxy being more preferred. Examples of the "substituent" of the "alkoxycarbonyl group of which alkoxy moiety is a C1-C6 linear or branched alkoxy group which may have a substituent(s)" represented by X in formula (1) include C1-C6 linear or branched alkoxy groups; e.g., methoxy, with no substituent being more preferred.

Examples of the "C1-C10 linear or branched alkyl group" of the "C1-C10 linear or branched alkyl group which may have a substituent(s)" represented by $R^1$, $R^2$, $R^3$, $R^4$, $R^5$ or $R^6$ in formula (1) include methyl, ethyl, n-propyl, isopropyl, n-butyl, tert-butyl, n-hexyl, thexyl, n-octyl, and n-decyl. Of these, preferred are C1-C8 linear or branched alkyl groups such as methyl, ethyl, n-propyl, isopropyl, n-butyl, tert-butyl, n-hexyl, thexyl, and n-octyl. More preferred examples are methyl, isopropyl, tert-butyl, and thexyl.

Examples of the "substituent" of the "C1-C10 linear or branched alkyl group which may have a substituent(s)" represented by $R^1$, $R^2$, $R^3$, $R^4$, $R^5$ or $R^6$ in formula (1) include C3-C6 cycloalkyl groups such as cyclopropyl, cyclobutyl, cyclopentyl, and cyclohexyl; C1-C3 alkoxy groups such as methoxy, ethoxy, and isopropoxy; C6-C14 aryl groups such as phenyl and naphthyl; hydroxy; amino; halogen atoms such as chlorine and bromine; cyano; and nitro.

Examples of the "C3-C6 cycloalkyl group" of the "C3-C6 cycloalkyl group which may have a substituent(s)" represented by $R^1$, $R^2$, $R^3$, $R^4$, $R^5$ or $R^6$ in formula (1) include cyclopropyl, cyclobutyl, cyclopentyl, and cyclohexyl group.

Examples of the "substituent" of the "C3-C6 cycloalkyl group which may have a substituent(S)" represented by $R^1$, $R^2$, $R^3$, $R^4$, $R^5$ or $R^6$ in formula (1) include C1-C3 linear or branched alkyl groups such as methyl, ethyl, and isopropyl group; C3-C6 cycloalkyl groups such as cyclopropyl, cyclobutyl, cyclopentyl, and cyclohexyl; C1-C3 alkoxy groups such as methoxy, ethoxy, and isopropoxy; C6-C14 aryl groups such as phenyl and naphthyl; hydroxy; amino; halogen atoms such as chlorine and bromine; cyano; and nitro.

Examples of the "C6-C14 aryl group" of the "C6-C14 aryl group which may have a substituent(s)" represented by $R^1$, $R^2$, $R^3$, $R^4$, $R^5$ or $R^6$ in formula (1) include phenyl and naphthyl, with phenyl being preferred.

Examples of the "substituent" of the "C6-C14 aryl group which may have a substituent(s)" represented by $R^1$, $R^2$, $R^3$, $R^4$, $R^5$ or $R^6$ in formula (1) include C1-C3 linear or branched alkyl groups such as methyl, ethyl, and isopropyl group; C3-C6 cycloalkyl groups such as cyclopropyl, cyclobutyl, cyclopentyl, and cyclohexyl; C1-C3 alkoxy groups such as methoxy, ethoxy, and isopropoxy; C6-C14 aryl groups such as phenyl and naphthyl; hydroxy; amino; halogen atoms such as chlorine and bromine; cyano; and nitro.

Examples of the groups $(R^1)(R^2)(R^3)Si$— and $(R^4)(R^5)(R^6)Si$—, which are identical to or different from one another and are represented by Y and Z in formula (1), include tert-butyldimethylsilyl, triisopropylsilyl, triisobutylsilyl, dimethyl-n-octylsilyl, dimethylthexylsilyl, trimethylsilyl, triethylsilyl, tri-n-propylsilyl, tri-n-butylsilyl, tri-n-hexylsilyl, n-propyldimethylsilyl, n-butyldimethylsilyl, isobutyldimethylsilyl, n-pentyldimethylsilyl, n-hexyldimethylsilyl, n-decyldimethylsilyl, (3,3-dimethylbutyl)dimethylsilyl, 1,2-dimethylpropyldimethylsilyl, di-tert-butylmethylsilyl, di-n-butylmethylsilyl, diethylisopropylsilyl, n-octyldiisopropylsilyl, n-octyldiisobutylsilyl, cyclohexyldimethylsilyl, dicyclohexylmethylsilyl, isopropyldiphenylsilyl, triphenylsilyl, dimethylphenylsilyl, tert-butyldiphenylsilyl, methyldiphenylsilyl, diphenyl(diphenylmethyl)silyl, p-toluoyldimethylsilyl, biphenyldimethylsilyl, biphenyldiisopropylsilyl, tri(2-biphenyl)silyl, tri(o-toluoyl)silyl, tri(2-methoxyphenyl)silyl, tribenzylsilyl, benzyldimethylsilyl, phenethyldimethylsilyl, (3-phenylpropyl)dimethylsilyl, p-(tert-butyl)phenethyldimethylsilyl, phenethyldiisopropylsilyl, neophyldimethylsilyl, bromomethyldimethylsilyl, chloromethyldimethylsilyl, 4-chlorobutyldimethylsilyl, (dichloromethyl)dimethylsilyl, 3-chloropropyldimethylsilyl, 3,3,3-trifluoropropyldimethylsilyl, 1H,1H,2H,2H-perfluoro-n-decyldimethylsilyl, 1H,1H,2H,2H-perfluoro-n-octyldimethylsilyl, 3,3,4,4,5,5,6,6,6-nonafluoro-n-hexyldimethylsilyl, bis(chloromethyl)methylsilyl, pentafluorophenyldimethylsilyl, pentafluorophenylpropyldimethylsilyl, 3,5-bis(trifluoromethyl)phenyldimethylsilyl, 2-acetoxyethyldimethylsilyl, 3-acetoxypropyldimethylsilyl, 3-methacryloxypropyldimethylsilyl, 3-cyanopropyldiisopropylsilyl, [3-(trimethylsiloxy)propyl]dimethylsilyl, n-butyldiisopropylsilyl, diisopropyl-n-propylsilyl, diisopropyl(2, 2-dimethylpropyl)silyl, (3-methylbutyl)diisopropylsilyl, (2-ethylbutyl)dicyclopropylsilyl, tert-amyldiethylsilyl, tert-butyldiisobutylsilyl, diethyl(3-methylpentan-3-yl)silyl, isobutyldiisopropylsilyl, diethyl(2-methylpentan-2-yl)silyl, cyclopropyldiisopropylsilyl, dicyclopropylisobutylsilyl, diisopropyl(3-methoxypropyl)silyl, (3-ethoxypropyl)diisopropylsilyl, [3-(tert-butyloxy)propyl]diisopropylsilyl, tert-butyldi(3-ethoxypropyl)silyl, and 3-phenoxypropyldimethylsilyl. In preferred $(R^1)(R^2)(R^3)Si$— and $(R^4)(R^5)(R^6)Si$—, one or two groups of $R^1$, $R^2$, and $R^3$, or of $R^4$, $R^5$, and $R^6$, which are identical to or different from one another, are C1-C4 linear or branched alkyl groups, and the remaining one or two groups, which are identical to or different from one another, are C2-C8 linear or branched alkyl groups or phenyl. Examples of such silyl groups include tert-butyldimethylsilyl, triethylsilyl, triisopropylsilyl, dimethyl-n-octylsilyl, dimethylphenylsilyl, dimethylthexylsilyl, and tert-butyldiphenylsilyl. In more referred $(R^1)(R^2)(R^3)Si$— and $(R^4)(R^5)(R^6)Si$—, two groups of $R^1$, $R^2$, and $R^3$, or of $R^4$, $R^5$, and $R^6$, which are identical to or different from one another, are C1-C3 linear or branched alkyl groups, and the remaining one group is a C2-C8 linear or branched alkyl group. Examples of such silyl groups include tert-butyldimethylsilyl, triethylsilyl, triisopropylsilyl, dimethyl-n-octylsilyl, and dimethylthexylsilyl group. In particularly more referred $(R^1)(R^2)(R^3)Si$— and $(R^4)(R^5)(R^6)Si$—, two groups of $R^1$, $R^2$, and $R^3$, or of $R^4$, $R^5$, and $R^6$, which are identical to or different from one another, are C1-C3 linear or branched alkyl groups, and the remaining one group is a C3-C6 branched alkyl group. Examples of such silyl groups include tert-butyldimethylsilyl, triisopropylsilyl, and dimethylthexylsilyl.

In formula (1), one of Y and Z is a hydrogen atom or a group $(R^1)(R^2)(R^3)Si$—, and the other represents a group $(R^4)(R^5)(R^6)Si$—. Preferably, one of Y and Z is a hydrogen atom, and the other is a group $(R^4)(R^5)(R^6)Si$—.

Preferably, in the compound of the present invention represented by formula (1), X is a hydrogen atom, an alkylcarbonyl group of which alkyl moiety is a C1-C6 linear or branched alkyl group which may have a substituent(s), or an alkoxycarbonyl group of which alkoxy moiety is a C1-C6 linear or branched alkoxy group which may have a substituent(s); one of Y and Z is a hydrogen atom or a group $(R^1)(R^2)(R^3)Si$— and the other is a group $(R^4)(R^5)(R^6)Si$—; and $R^1$, $R^2$, $R^3$, $R^4$, $R^5$, and $R^6$, which may be identical to or different from one another, each are a C1-C10 linear or branched alkyl group which may have a substituent(s), a C3-C6 cycloalkyl group which may have a substituent(s), or a C6-C14 aryl group which may have a substituent(s).

More preferably, in formula (1), X is a hydrogen atom, an alkylcarbonyl group of which alkyl moiety is a C1-C6 linear or branched alkyl group which may have, as a substituent(s), an amino group mono- or di-substituted by a C1-C6 linear or branched alkyl group, or an alkoxycarbonyl group of which alkoxy moiety is a C1-C6 linear or branched alkoxy group; one of Y and Z is a hydrogen atom or a group $(R^1)(R^2)(R^3)Si$— and the other is a group $(R^4)(R^5)(R^6)Si$—; and $R^1$, $R^2$, $R^3$, $R^4$, $R^5$, and $R^6$, which may be identical to or different from one another, each are a C1-C10 linear or branched alkyl group, a C3-C6 cycloalkyl group, or a C6-C14 aryl group.

Still more preferably, in formula (1), X is a hydrogen atom, an alkylcarbonyl group of which alkyl moiety is a C1-C6 linear or branched alkyl group which may have a dimethylamino group as a substituent(s), or an alkoxycarbonyl group of which alkoxy moiety is a C1-C6 linear or branched alkoxy group; one of Y and Z is a hydrogen atom or a group $(R^1)(R^2)(R^3)Si$— and the other is a group $(R^4)(R^5)(R^6)Si$—; and $R^1$, $R^2$, $R^3$, $R^4$, $R^5$, and $R^6$, which may be identical to or different from one another, each are a C1-C10 linear or branched alkyl group, a C3-C6 cycloalkyl group, or a C6-C14 aryl group.

Still more preferably, in formula (1), X is a hydrogen atom; one of Y and Z is a hydrogen atom or a group $(R^1)(R^2)(R^3)Si$— and the other is a group $(R^4)(R^5)(R^6)Si$—; and $R^1$, $R^2$, $R^3$, $R^4$, $R^5$, and $R^6$, which may be identical to or different from one another, each are a C1-C10 linear or branched alkyl group, a C3-C6 cycloalkyl group, or a C6-C14 aryl group.

Still more preferably, in formula (1), X is a hydrogen atom; one of Y and Z is a hydrogen atom or a group $(R^1)(R^2)(R^3)Si$— and the other is a group $(R^4)(R^5)(R^6)Si$—; and $R^1$, $R^2$, $R^3$, $R^4$, $R^5$, and $R^6$, which may be identical to or different from one another, each are a C1-C8 linear or branched alkyl group or a phenyl group.

Still more preferably, in formula (1), X is a hydrogen atom; one of Y and Z is a hydrogen atom and the other is a group $(R^4)(R^5)(R^6)Si$—; and $R^4$, $R^5$, and $R^6$, which may be identical to or different from one another, each are a C1-C8 linear or branched alkyl group or a phenyl group.

Still more preferably, in formula (1), X is a hydrogen atom; one of Y and Z is a hydrogen atom and the other is a tert-butyldimethylsilyl group, a triethylsilyl group, a triisopropylsilyl group, a dimethyl-n-octylsilyl group, a dimethylphenylsilyl group, a dimethylthexylsilyl group, or a tert-butyldiphenylsilyl group.

Specific examples of such preferred compounds include the following 3'-ethynylcytidine derivatives (1) to (17) or salts thereof:

(1) 1-[5-O-(tert-butyldimethylsilyl)-3-C-ethynyl-β-D-ribofuranosyl]cytosine,
(2) 1-[5-O-triethylsilyl-3-C-ethynyl-β-D-ribofuranosyl]cytosine,
(3) 1-[5-O-triisopropylsilyl-3-C-ethynyl-β-D-ribofuranosyl]cytosine,
(4) 1-[5-O-(dimethyl-n-octylsilyl)-3-C-ethynyl-β-D-ribofuranosyl]cytosine,
(5) 1-[5-O-dimethylphenylsilyl-3-C-ethynyl-β-D-ribofuranosyl]cytosine,
(6) 1-[5-O-dimethylthexylsilyl-3-C-ethynyl-β-D-ribofuranosyl]cytosine,
(7) 1-[5-O-(tert-butyldiphenylsilyl)-3-C-ethynyl-β-D-ribofuranosyl]cytosine,
(8) 1-[2,5-bis-O-(tert-butyldimethylsilyl)-3-C-ethynyl-1-β-D-ribofuranosyl]cytosine,
(9) 1-[2-O-(tert-butyldimethylsilyl)-3-C-ethynyl-1-β-D-ribofuranosyl]cytosine,
(10) 1-(2,5-bis-O-triisopropylsilyl-3-C-ethynyl-1-β-D-ribofuranosyl)cytosine,
(11) 1-(2-O-triisopropylsilyl-3-C-ethynyl-1-β-D-ribofuranosyl)cytosine,
(12) 1-(2,5-bis-O-dimethylthexylsilyl-3-C-ethynyl-1-β-D-ribofuranosyl)cytosine,
(13) 1-(2-O-dimethylthexylsilyl-3-C-ethynyl-1-β-D-ribofuranosyl)cytosine,
(14) 1-[5-O-(tert-butyldimethylsilyl)-3-C-ethynyl-β-D-ribofuranosyl]-4-N-heptanoylcytosine,
(15) 1-[5-O-(tert-butyldimethylsilyl)-3-C-ethynyl-β-D-ribofuranosyl]-4-N-(tert-butoxycarbonyl)cytosine,
(16) 1-[5-O-(tert-butyldimethylsilyl)-3-C-ethynyl-β-D-ribofuranosyl]-4-N-(N,N-dimethylglycyl)cytosine, and
(17) 1-[5-O-(triisopropylsilyl)-3-C-ethynyl-β-ribofuranosyl]-4-N-(N,N-dimethylglycyl)cytosine.

Specific examples of such preferred compounds include the following 3'-ethynylcytidine derivatives or salts thereof:
(1) 1-[5-O-(tert-butyldimethylsilyl)-3-C-ethynyl-1-β-D-ribofuranosyl]cytosine, (3) 1-(5-O-triisopropylsilyl-3-C-ethynyl-1-β-D-ribofuranosyl)cytosine,
(6) 1-(5-O-dimethylthexylsilyl-3-C-ethynyl-1-β-D-ribofuranosyl)cytosine,
(9) 1-[2-O-(tert-butyldimethylsilyl)-3-C-ethynyl-1-β-D-ribofuranosyl]cytosine,
(11) 1-(2-O-triisopropylsilyl-3-C-ethynyl-1-β-D-ribofuranosyl)cytosine, and
(13) 1-(2-O-dimethylthexylsilyl-3-C-ethynyl-1-β-D-ribofuranosyl)cytosine.

No particular limitation is imposed on the salt of the 3'-ethynylcytidine derivative of the present invention, so long as the salt is pharmaceutically acceptable. Examples of the salt include mineral acid salts such as hydrochloride, hydrobromide, sulfate, nitrate, and phosphate; and organic acid salts such as acetate, propionate, tartrate, fumarate, maleate, malate, citrate, methanesulfonate, p-toluenesulfonate, and trifluoroacetate. Depending on the identity of the substituent(s), the 3'-ethynylcytidine derivative of the present invention may form optical isomers or geometrical isomers, and the present invention encompasses such optical isomers and geometrical isomers, with the proviso that the sterostructure of the 3'-ethynylcytidine skeleton is maintained as specified in formula (1). These isomers may be used after being resolved or used as a mixture. The 3'-ethynylcytidine derivative of the present invention also encompasses amorphous species, polymorphisms, and solvates such as hydrates.

The 3'-ethynylcytidine derivative or a salt thereof of the present invention may be produced in accordance with the following reaction scheme including Steps 1 to 7:

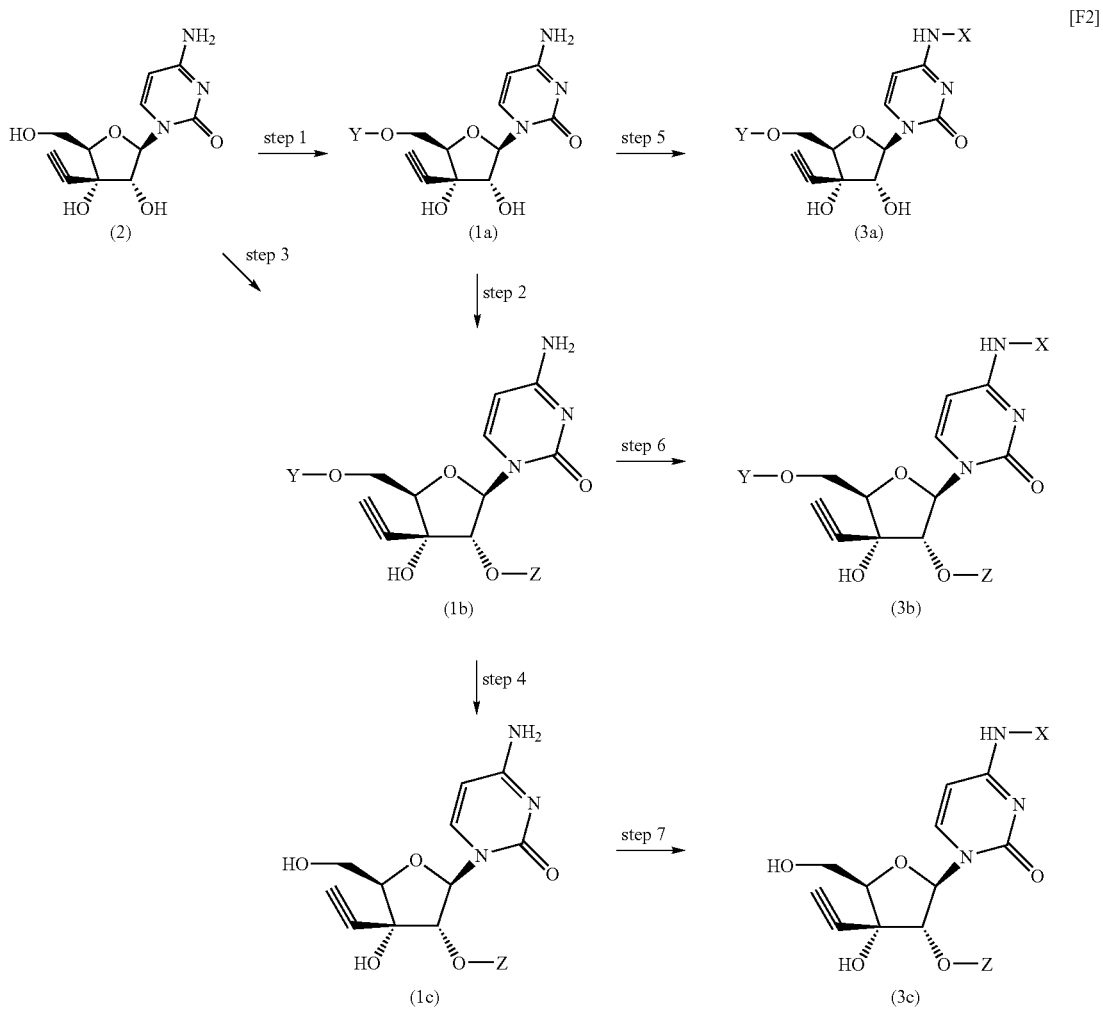

[F2]

(wherein X, Y, and Z have the same meanings as defined above).

(Step 1)

In Step 1, a 3'-ethynylcytidine represented by formula (2) or a salt thereof is reacted with a generally known tri-substituted silylating agent such as a tri-substituted silyl halide, a tri-substituted silyl triflate, or a tri-substituted silylacetamide, represented by $(R^1)(R^2)(R^3)Si-W$ or $(R^4)(R^5)(R^6)Si-W$ (wherein W represents a halogen atom, a trifluoromethanesulfonyloxy group, an acetamino group, or the like, and $R^1$ to $R^6$ have the same meanings as defined above), whereby a compound represented by formula (1a) can be produced.

The reaction may be performed in accordance with a generally known method. No particular limitation is imposed on the solvent employed in the reaction, and any solvent may be employed so long as it is inert to the reaction. Examples of the solvent include dichloromethane, chloroform, ethyl acetate, tetrahydrofuran, dioxane, diethyl ether, benzene, toluene, N,N-dimethylformamide, and dimethyl sulfoxide. These solvents may be used singly or in combination. If required, the reaction may be performed in the presence of a base. Examples of the base employed include organic amines such as imidazole, 1-methylimidazole, trimethylamine, triethylamine, tripropylamine, diisopropylethylamine, N-methylmorpholine, pyridine, 4-(N,N-dimethylamino)pyridine, lutidine, and collidine; and inorganic bases such as sodium hydrogen carbonate, sodium carbonate, and potassium carbonate. The base per se may be employed as a solvent.

The tri-substituted silyl halide which is employed in the reaction and represented by $(R^1)(R^2)(R^3)Si$—W or $(R^4)(R^5)(R^6)Si$—W may be produced through a generally known method. For example, trihalogenosilane, monoalkyldihalogenosilane, or dialkylmonohalogenosilane is reacted with an alkyllithium or a Grignard reagent of interest, to thereby form a tri-substituted silane represented by $(R^1)(R^2)(R^3)Si$—H or $(R^4)(R^5)(R^6)$ Si—H, which is then reacted with an electrophilic reagent such as N-bromosuccinimide or N-chlorosuccinimide. In the production of a tri-substituted silane represented by $(R^1)(R^2)(R^3)$ Si—H or $(R^4)(R^5)(R^6)Si$—H, an additive such as copper bromide may be used. If required, the tri-substituted silane represented by $(R^1)(R^2)(R^3)Si$—H or $(R^4)(R^5)(R^6)Si$—H and the tri-substituted silyl halide represented by $(R^1)(R^2)(R^3)Si$—W or $(R^4)(R^5)(R^6)Si$—W may be isolated/purified. Alternatively, the produced silane compound and silyl halide may be used in Step 1 without performing purification.

In the reaction, with respect to 1 mol of the compound represented by formula (2), the aforementioned $(R^1)(R^2)(R^3)Si$—W or $(R^4)(R^5)(R^6)Si$—W is used in an amount of about 0.5 to about 10 mol, preferably about 1 to about 5 mol, and the base is used in an amount of about 0.5 to about 100 mol, preferably about 1 to about 10 mol. The reaction temperature is −30 to 100° C., preferably 0 to 30° C., and the reaction time is 0.1 to 100 hours, preferably 1 to 20 hours. If required, the compound represented by formula (1a) produced through the reaction may be isolated/purified. Alternatively, the compound may be used in a subsequent step without performing purification.

(Step 2)

In Step 2, the 3'-ethynylcytidine derivative represented by formula (1a) is reacted with the aforementioned tri-substituted silylating agent represented by $(R^1)(R^2)(R^3)Si$—W or $(R^4)(R^5)(R^6)Si$—W in the presence of a base, to thereby produce a compound represented by formula (1b). The reaction may be performed in a manner similar to that of Step 1.

(Step 3)

Similar to Step 1, in Step 3, the 3'-ethynylcytidine represented by formula (2) is reacted with the aforementioned tri-substituted silylating agent represented by $(R^1)(R^2)(R^3)Si$—W or $(R^4)(R^5)(R^6)Si$—W in the presence of a base, to thereby produce a compound represented by formula (1b). The reaction temperature is −30 to 150° C., preferably 0 to 100° C., and the reaction time is 0.1 to 100 hours, preferably 1 to 40 hours. If required, the compound represented by formula (1b) produced through the reaction may be isolated/purified. Alternatively, the compound may be used in a subsequent step without performing purification.

(Step 4)

In Step 4, a compound represented by formula (1c) is produced from the 3'-ethynylcytidine derivative represented by formula (1b) in an acidic medium. No particular limitation is imposed on the acid so long as it can remove the substituent Y. Examples of the acid include mineral acids such as hydrochloric acid, hydrobromic acid, sulfuric acid, nitric acid, and phosphoric acid; and organic acids such as trifluoroacetic acid, acetic acid, propionic acid, formic acid, methanesulfonic acid, and p-toluenesulfonic acid. These acids may be mixed with water. If required, a solvent may be used. Examples of the solvent include dichloromethane, chloroform, ethyl acetate, tetrahydrofuran, dioxane, diethyl ether, benzene, toluene, N,N-dimethylformamide, dimethyl sulfoxide, methanol, ethanol, n-propanol, isopropanol, and water. These solvents may be used singly or in combination. The reaction temperature is −30 to 150° C., preferably 0 to 100° C., and the reaction time is 0.1 to 100 hours, preferably 1 to 20 hours.

(Step 5)

In Step 5, the 3'-ethynylcytidine derivative represented by formula (1a) is modified with a group X, to thereby produce a compound represented by formula (3a).

In the case where the group X is a carbonyl group having an alkyl group, the modification is performed through condensation with an acid halide X—V (wherein V denotes a halogen atom), an acid anhydride X—O—X, or a carboxylic acid X—OH. No particular limitation is imposed on the solvent employed in the reaction, and any solvent may be employed so long as it is inert to the reaction. Examples of the solvent include dichloromethane, chloroform, ethyl acetate, tetrahydrofuran, dioxane, diethyl ether, benzene, toluene, N,N-dimethylformamide, dimethyl sulfoxide, and water. These solvents may be used singly or in combination. When the acid halide X—V or the acid anhydride X—O—X is employed, a base may be used. Examples of the base employed include organic amines such as trimethylamine, triethylamine, tripropylamine, diisopropylethylamine, N-methylmorpholine, pyridine, 4-(N,N-dimethylamino)pyridine, lutidine, and collidine; and inorganic bases such as sodium hydrogen carbonate, sodium carbonate, and potassium carbonate. The base per se may be employed as a solvent. No particular limitation is imposed on the condensation reaction with the carboxylic acid X—OH, so long as the reaction generally yields amide from carboxylic acid and amine. For example, a method employing a mixed acid anhydride, a method employing a condensing agent, or the like method may be employed. Examples of the base used in the method employing a mixed acid anhydride include organic amines such as trimethylamine, triethylamine, tripropylamine, diisopropylethylamine, N-methylmorpholine, pyridine, 4-(N,N-dimethylamino)pyridine, lutidine, and collidine; and inorganic bases such as sodium hydrogen carbonate, sodium carbonate, and potassium carbonate. The base per se may be employed as a solvent. As the reagent for forming a mixed acid anhydride with the carboxylic acid X—OH, isobutyl chlorocarbonate, pivaloyl chloride, etc. may be employed. When a condensing agent is used, carbodiimide compounds such as dicyclohexylcarbodiimide or 1-ethyl-3-(3-dimethylaminopropyl) carbodiimide hydrochloride; or 1,1'-carbonyldiimidazole or a similar compound may be employed. Examples of condensing aids include 1-hydroxybenzotriazole hydrate, N-hydroxysuccinimide, N-hydroxy-5-norbornene-2,3-dicarboximide, and 4-(N,N-dimethylamino)pyridine. If required, a base may be used during reaction. Examples of the base employed include organic amines such as trimethylamine, triethylamine, tripropylamine, diisopropylethylamine, N-methylmorpholine, pyridine, 4-(N,N-dimethylamino)pyridine, lutidine, and collidine; and inorganic bases such as sodium hydrogen carbonate, sodium carbonate, and potassium carbonate. The base per se may be employed as a solvent.

In the reaction, when the acid halide X—V or the acid anhydride X—O—X is employed, the acid halide X—V or the acid anhydride X—O—X is used in an amount of about 0.5 to about 20 mol, preferably about 1 to about 10 mol, with respect to 1 mol of the compound represented by formula (1a), and a base is used in an amount of 0 to about 100 mol, preferably about 1 to about 20 mol. The reaction temperature is −30 to 100° C., preferably −10 to 30° C., and the reaction time is 0.1 to 100 hours, preferably 1 to 72 hours. When condensation with the carboxylic acid X—OH is performed through the mixed acid anhydride method, with respect to 1 mol of the compound represented by formula (1a), the carboxylic acid X—OH is used in an amount of about 0.5 to about 20 mol, preferably about 1 to about 10 mol; a reagent for forming a mixed acid anhydride is used in an amount of about 0.5 to about 20 mol, preferably, about 1 to about 10 mol; and a base is used in an amount of about 0.5 to about 100 mol, preferably about 1 to about 20 mol. The reaction temperature is −30 to 100° C., preferably −10 to 30° C., and the reaction time is 0.1 to 100 hours, preferably 1 to 72 hours. When the condensing agent is employed, with respect to 1 mol of the compound represented by formula (1a), the carboxylic acid X—OH is used in an amount of about 0.5 to about 20 mol, preferably about 1 to about 10 mol; the condensing agent is used in an amount of about 0.5 to about 20 mol, preferably about 1 to about 10 mol; a condensing aid is used in an amount of about 0.1 to about 40 mol, preferably about 1 to about 10 mol; and a base is used in an amount of 0 to about 100 mol, preferably 0 to about 20 mol. The reaction temperature is −30 to 100° C., preferably −10 to 30° C., and the reaction time is 0.1 to 100 hours, preferably 1 to 72 hours. If required, the compound represented by formula (3a) produced through any of the methods may be isolated/purified. Alternatively, the compound may be used in a subsequent step without performing purification.

When the group X is an alkoxycarbonyl group, no particular limitation is imposed on the reaction in Step 5 so long as it is a routine reaction. In one exemplary method, a 3'-ethynylcytidine derivative represented by formula (1a) or a salt thereof is reacted with a dialkyl dicarbonate, an alkyl haloformate, an alkyl (p-nitrophenyl)carbonate, a 1-H-imidazole-1-carboxylic acid alkyl ester, etc. which are represented by X-Q (wherein Q represents an alkoxycarbonyloxy group X-O, a halogen atom, a 4-nitrophenyloxy group, a 1-H-imidazol-1-yl group, etc.). The reaction may be performed in accordance with a generally known method. No particular limitation is imposed on the solvent employed in the reaction, and any solvent may be employed so long as it is inert to the reaction. Examples of the solvent include dichloromethane, chloroform, ethyl acetate, tetrahydrofuran, dioxane, diethyl ether, benzene, toluene, N,N-dimethylformamide, N,N-dimethylacetamide, dimethyl sulfoxide, and water. These solvents may be used singly or in combination. If required, the reaction may be performed in the presence of a base. Examples of the base employed include organic amines such as imidazole, 1-methylimidazole, trimethylamine, triethylamine, tripropylamine, diisopropylethylamine, N-methylmorpholine, pyridine, 4-(N,N-dimethylamino)pyridine, lutidine, and collidine; and inorganic bases such as sodium hydrogen carbonate, sodium carbonate, and potassium carbonate. The base per se may be employed as a solvent.

The alkyl haloformate X-Q employed in the reaction may be prepared through a generally known method. For example, the haloformate can be produced through reaction between triphosgene and a corresponding alkyl alcohol. Similarly, the alkyl (p-nitrophenyl)carbonate X-Q employed in the reaction may be prepared through a generally known method. For example, the carbonate can be prepared through reaction between p-nitrophenyl chloroformate and a corresponding alkyl alcohol. Also, the 1-H-imidazole-1-carboxylic acid alkyl ester X-Q employed in the reaction may be prepared through a generally known method. For example, the ester can be prepared through reaction between 1,1'-carbonyldiimidazole and a corresponding alkyl alcohol. If required, the alkyl haloformate, alkyl (p-nitrophenyl)carbonate, and 1-H-imidazole-1-carboxylic acid alkyl ester represented by X-Q may be isolated/purified. Alternatively, these compounds may be employed in Step 5 without performing purification.

In the reaction, with respect to 1 mol of the compound represented by formula (1a), the aforementioned compound X-Q is used in an amount of about 0.5 to about 20 mol, preferably about 1 to about 10 mol; and a base is used in an amount of about 0.5 to about 100 mol, preferably about 1 to about 20 mol. The reaction temperature is −30 to 100° C., preferably −10 to 30° C., and the reaction time is 0.1 to 100 hours, preferably 1 to 72 hours. If required, the compound represented by formula (3a) produced through the reaction may be isolated/purified. Alternatively, the compound may be used in a subsequent step without performing purification.

(Step 6)

Similar to Step 5, in Step 6, the 3'-ethynylcytidine derivative represented by formula (1b) is modified with a group X, to thereby produce a compound represented by formula (3b).

(Step 7)

Similar to Step 5, in Step 7, the 3'-ethynylcytidine derivative represented by formula (1c) is modified with a group X, to thereby produce a compound represented by formula (3c).

The thus-produced compound of the present invention may be transformed into salts thereof, particularly pharmaceutically acceptable salts, through a generally known method.

The compound or a salt thereof of the present invention may be isolated and purified through a generally known separation/purification method such as concentration, extraction with solvent, filtration, recrystallization, or a chromatographic technique.

As described by way of Examples, the compound or a salt thereof of the present invention exhibits excellent anti-tumor effect when orally administered. Thus, it is a useful drug, particularly an anti-tumor drug, for human and mammals.

Upon use of the compound of present invention as a drug, the compound is blended with a pharmaceutically acceptable carrier, and a variety of administration forms may be chosen in accordance with prophylactic and treatment purposes. Any administration forms may be employed, and examples include oral drugs, injections, suppositories, ointments, and patches. Of these, oral forms are preferably employed. These drug forms may be produced through any pharmaceutical techniques known in the art.

The pharmaceutically acceptable carrier to be employed may be any organic and inorganic carrier substances which are customarily employed as materials for drug preparation. In solid drugs, the carrier is incorporated in the form of a vehicle, a lubricant, a binder, a disintegrant, or a similar additive. In liquid drugs, the carrier is incorporated as a solvent, a dissolution aid, a suspending agent, a tonicity agent, a buffer, a soothing agent, or a similar additive. Other additives such as a preservative, an antioxidant, a colorant, and a sweetening agent may also be incorporated in accordance with needs.

In preparation of a oral solid drug, the compound of the present invention is blended with a vehicle and optional additives such as a binder, a disintegrant, a lubricant, a colorant, and a sweetening/flavoring agent, and the mixture is formed into tablets, coated tablets, granules, powder, capsules, etc. through a routine method. These additives may be those generally employed in the art, and examples include lactose, sucrose, sodium chloride, glucose, starch, calcium carbonate, kaolin, microcrystalline cellulose, and silicic acid (vehicles);

water, ethanol, propanol, simple syrup, glucose liquid, starch liquid, gelatin liquid, carboxymethylcellulose, hydroxypropylcellulose, hydroxypropylstarch, methylcellulose, ethylcellulose, shellac, calcium phosphate, and polyvinylpyrrolidone (binders); dry starch, sodium alginate, agar powder, sodium hydrogen carbonate, calcium carbonate, sodium lauryl sulfate, stearic acid monoglyceride, and lactose (disintegrants); purified talc, stearic acid salts, borax, and polyethylene glycol (lubricants); titanium oxide and iron oxide (colorants); and sucrose, orange peel, citric acid, and tartaric acid (sweetening/flavoring agents).

In preparation of a oral liquid drug, the compound of the present invention is blended with additives such as a sweetening agent, a buffer, a stabilizer, and a flavoring agent, and the mixture is formed into a oral liquid drug, a syrup, an elixir, etc., through a routine method. In this case, the sweetening/flavoring agent may be the same as described above. Examples of the buffer include sodium citrate, and examples of the stabilizer include tragacanth, acacia, and gelatin.

In preparation of an injection, the compound of the present invention is blended with additives such as a pH-regulator, a buffer, a stabilizer, a tonicity agent, and a local anesthetic, and the mixture is formed into subcutaneous, intramuscular, and intravenous injections, through a routine method. In this case, examples of the pH-regulator and the buffer include sodium citrate, sodium acetate, and sodium phosphate, and examples of the stabilizer include sodium pyrosulfite, EDTA, thioglycolic acid, and thiolactic acid. Examples of the local anesthetic include procaine hydrochloride and lidocaine hydrochloride. Examples of the tonicity agent include sodium chloride and glucose.

In preparation of a suppository drug, the compound of the present invention is blended with a carrier for drug preparation known in the art, such as polyethylene glycol, lanolin, cacao butter, and fatty acid triglyceride and an optional surfactant such as Tween (registered trademark), and the mixture is formed into suppositories through a routine method.

In preparation of an ointment, the compound of the present invention is blended, in accordance with needs, with generally employed additives such as a base, a stabilizer, a moisturizer, a preservative, etc., and the mixture is mixed and formed into a drug through a routine method. Examples of the ointment base include liquid paraffin, white vaseline, white beeswax, octyl dodecyl alcohol, and paraffin. Examples of the preservative include methyl p-hydroxybenzoate, ethyl p-hydroxybenzoate, and propyl p-hydroxybenzoate.

In preparation of a patch drug, the aforementioned ointment, cream, gel, paste, or a similar material is applied to a customary support through a routine method. Examples of suitable supports include woven and non-woven fabric of cotton, staple fiber, or chemical fiber; and films and foamed sheet made of soft vinyl chloride, polyethylene, or polyurethane.

The unit dose of the compound of the present invention which is to be incorporated in any of the aforementioned drugs varies in accordance with the condition of the patients to whom the compound of the invention is to be administered, the form of drugs, or other factors. Generally, the unit dose is preferably about 0.05 to 1,000 mg for oral drugs, about 0.01 to 500 mg for injections, and about 1 to 1,000 mg for suppositories. The daily dose of a drug having any of the aforementioned drug forms varies depending on the condition, body weight, age, sex, etc., of the patient, and therefore, it cannot necessarily be determined immediately. However, generally, the daily dose for an adult is about 0.05 to 5,000 mg, preferably 0.1 to 1,000 mg. The unit dose is preferably administered once a day or in a divided manner of about twice to about four times per day.

Examples of the diseases (in the case of malignant tumors) which can be cured through administration of a drug containing the compound of the present invention include head and neck cancer, esophageal cancer, gastric cancer, colon cancer, rectal cancer, liver cancer, gallbladder/bile duct cancer, pancreatic cancer, lung cancer, breast cancer, ovarian cancer, cervical cancer, uterine corpus cancer, renal cancer, bladder cancer, prostatic cancer, testicular tumor, osteosarcoma and soft tissue sarcoma, leukemia, malignant lymphoma, multiple myeloma, skin cancer, and brain tumor.

EXAMPLES

The present invention will next be described in detail with reference to Comparative Examples, Examples (working examples), Pharmacological Test Examples, and Preparation Examples. However, any of these should not be construed as limiting the invention thereto.

Example 1

1-[5-O-(tert-Butyldimethylsilyl)-3-C-ethynyl-β-D-ribofuranosyl]cytosine (Compound 1)

tert-Butyldimethylsilylchloride (12.5 g, 82.5 mmol) was gradually added under ice-cooling to a solution of 3'-ethynyl-cytidine (hereinafter referred to as ECyd) (20 g, 75 mmol) and imidazole (12.8 g, 188 mmol) in N,N-dimethylformamide (hereinafter referred to as DMF) (75 mL), and the mixture was stirred for 5 hours at room temperature. After completion of reaction, the solvent was evaporated under reduced pressure, and ethyl acetate was added to the residue. The mixture was washed with saturated aqueous sodium hydrogen carbonate (100 mL) and saturated brine (100 mL) and dried with magnesium sulfate. Magnesium sulfate was removed through filtration. The filtrate was stirred at room temperature, and precipitated crystals were collected through filtration, to thereby yield Compound 1 (11.5 g, 52%).

Example 2

1-[5-O-Triethylsilyl-3-C-ethynyl-β-D-ribofuranosyl]cytosine (Compound 2)

The procedure of Example 1 was repeated, except that triethylsilylchloride was employed instead of tert-butyldimethylsilylchloride employed in Example 1, whereby Compound 2 was synthesized.

Example 3

1-[5-O-Triisopropylsilyl-3-C-ethynyl-β-D-ribofuranosyl]cytosine (Compound 3)

The procedure of Example 1 was repeated, except that triisopropylsilylchloride was employed instead of tert-butyldimethylsilylchloride employed in Example 1, whereby Compound 3 was synthesized.

Example 4

1-[5-O-(Dimethyl-n-octylsilyl)-3-C-ethynyl-β-D-ribofuranosyl]cytosine (Compound 4)

The procedure of Example 1 was repeated, except that dimethyl-n-octylsilylchloride was employed instead of tert-butyldimethylsilylchloride employed in Example 1, whereby Compound 4 was synthesized.

Example 5

1-[5-O-Dimethylphenylsilyl-3-C-ethynyl-β-D-ribofuranosyl]cytosine (Compound 5)

The procedure of Example 1 was repeated, except that dimethylphenylsilylchloride was employed instead of tert-butyldimethylsilylchloride employed in Example 1, whereby Compound 5 was synthesized.

Example 6

1-[5-O-Dimethylthexylsilyl-3-C-ethynyl-β-D-ribofuranosyl]cytosine (Compound 6)

The procedure of Example 1 was repeated, except that dimethylthexylsilylchloride was employed instead of tert-butyldimethylsilylchloride employed in Example 1, whereby Compound 6 was synthesized.

Example 7

1-[5-O-(tert-Butyldiphenylsilyl)-3-C-ethynyl-β-D-ribofuranosyl]cytosine (Compound 7)

The procedure of Example 1 was repeated, except that tert-butyldiphenylsilylchloride was employed instead of tert-butyldimethylsilylchloride employed in Example 1, whereby Compound 7 was synthesized.

Example 8

1-[2,5-bis-O-(tert-Butyldimethylsilyl)-3-C-ethynyl-1-β-D-ribofuranosyl]cytosine (Compound 8)

ECyd (5.00 g, 18.7 mmol) was dissolved in DMF (19 mL), and imidazole (3.82 g, 56.1 mmol) and tert-butyldimethylsilylchloride (6.20 g, 41.1 mmol) were added to the solution, followed by stirring for 4 hours at room temperature under a stream of nitrogen. The solvent was evaporated, and the residue was dissolved in ethyl acetate. The solution was washed with water and saturated brine. The organic layer was dried over sodium sulfate anhydrate, and the solvent was evaporated. The residue was purified through silica gel column chromatography (0-5% methanol/chloroform). Subsequently, the product was crystallized from hexane/ether, to thereby yield Compound 8 (6.36 g, 12.8 mmol, 69%) as a white solid.

Example 9

1-[2-O-(tert-Butyldimethylsilyl)-3-C-ethynyl-1-β-D-ribofuranosyl]cytosine (Compound 9)

Compound 8 (2.00 g, 4.03 mmol) was dissolved in tetrahydrofuran (hereinafter referred to as THF) (20 mL), and 80% aqueous trifluoroacetic acid (20 mL) was added to the solution, followed by stirring for 1 hour at room temperature. The reaction mixture was concentrated under reduced pressure, and the residue was co-boiled three times with ethanol, and the product was partitioned between ethyl acetate and water. The organic layer was washed with saturated aqueous sodium hydrogen carbonate and saturated brine, and then dried over sodium sulfate anhydrate. The solvent was evaporated, and the residue was purified through silica gel column chromatography (0-6% methanol/chloroform), and then crystallized from hexane/ether, to thereby yield Compound 9 (645 mg, 1.69 mmol, 42%) as a white solid.

Example 10

1-(2,5-bis-O-Triisopropylsilyl-3-C-ethynyl-1-β-D-ribofuranosyl)cytosine (Compound 10)

ECyd (5.00 g, 18.7 mmol) was dissolved in DMF (19 mL), and imidazole (5.73 g, 84.2 mmol) and triisopropylsilylchloride (12.8 mL, 59.8 mmol) were added to the solution, followed by stirring overnight at room temperature under a stream of nitrogen. The solvent was evaporated, and the residue was dissolved in ethyl acetate. The solution was washed with water and saturated brine. The organic layer was dried over sodium sulfate anhydrate, and the solvent was evaporated. The residue was purified through silica gel column chromatography (0-6% methanol/chloroform), to thereby yield Compound 10 (5.05 g, 8.70 mmol, 46%) as a colorless foam.

Example 11

1-(2-O-Triisopropylsilyl-3-C-ethynyl-1-β-D-ribofuranosyl)cytosine (Compound 11)

ECyd (4.01 g, 15 mmol) was dissolved in DMF (30 mL), and imidazole (6.39 g, 93.9 mmol) and triisopropylsilylchloride (8.02 mL, 37.5 mmol) were added to the solution, followed by stirring under a stream of nitrogen for 3 hours at room temperature and then for 24 hours at 50° C. The reaction mixture was partitioned between ethyl acetate and water, and the organic layer was washed five times with water and then dried over sodium sulfate anhydrate. The solvent was evaporated, and 10.1 g of the residue was obtained. 1.9 g of the obtained residue was dissolved in methanol (5.2 mL), and water (0.58 mL) and methanesulfonic acid (347 μL, 4.76 mmol) were added to the solution, followed by stirring for 1 hour at 40° C. The reaction mixture was partitioned between ethyl acetate and saturated aqueous sodium hydrogen carbonate, and the organic layer was washed with water and saturated brine and then dried over sodium sulfate anhydrate. The solvent was evaporated, and the residue was crystallized from tert-butyl methyl ether-water-diisopropyl ether. The formed crystals were again crystallized from methanol-water-triethylamine, to thereby yield Compound 11 (961 mg, 80%) as a white solid.

Example 12

1-(2,5-bis-O-Dimethylthexylsilyl-3-C-ethynyl-1-β-D-ribofuranosyl)cytosine (Compound 12)

ECyd (2.67 g, 10 mmol) was dissolved in DMF (100 mL), and imidazole (4.50 g, 66 mmol) and dimethylthexylsilylchloride (5.90 g, 33 mmol) were added to the solution, followed by stirring for 48 hours at room temperature under a stream of nitrogen. The solvent was evaporated, and the residue was dissolved in ethyl acetate. The solution was washed with water and saturated brine. The organic layer was dried over sodium sulfate anhydrate, and the solvent was evaporated. The residue was purified through silica gel column chromatography (0-3% methanol/chloroform), to thereby yield Compound 12 (4.34 g, 79%) as a colorless foam.

Example 13

1-(2-O-Dimethylthexylsilyl-3-C-ethynyl-1-β-D-ribofuranosyl)cytosine trifluoroacetic acid salt (Compound 13)

Compound 12 (2.0 g, 3.6 mmol) was dissolved in THF (20 mL), and 80% aqueous trifluoroacetic acid (20 mL) was added to the solution, followed by stirring for 4 hours at room temperature. The reaction mixture was concentrated under reduced pressure, and the residue was co-boiled three times with ethanol. Chloroform was added to the co-boiling residue, and the white solid that precipitated was collected through filtration, to thereby yield Compound 13 (1.54 g, 81%) as a white solid.

Example 14

1-(2-O-Dimethylthexylsilyl-3-C-ethynyl-1-β-D-ribofuranosyl)cytosine (Compound 14)

Compound 13 (1.0 g, 1.9 mmol) was dissolved in 5% methanol/chloroform solvent mixture (100 mL), and the solution was washed with saturated aqueous sodium hydrogen carbonate. The organic layer was washed with water and saturated brine and then dried over sodium sulfate anhydrate. The solvent was evaporated, and the residue was crystallized from hexane/ether, to thereby yield Compound 14 (690 mg, 1.68 mmol, 88%) as a white solid.

Example 15

1-[5-O-(tert-Butyldimethylsilyl)-3-C-ethynyl-β-D-ribofuranosyl]-4-N-heptanoylcytosine (Compound 15)

Compound 1 (1.27 g, 3.3 mmol) and heptanoic acid anhydride (1.8 mL, 6.8 mmol) were added to a solvent mixture of dioxane (14 mL) and water (5 mL), and the mixture was stirred for one day at 100° C. After completion of reaction, the reaction mixture was extracted with ethyl acetate (50 mL), and the organic layer was neutralized with 1N aqueous sodium hydroxide. The resultant mixture was washed with saturated brine (50 mL) and then dried over magnesium sulfate. Magnesium sulfate was removed through filtration, and the solvent was evaporated under reduced pressure. The residue was purified through silica gel chromatography (4% methanol/chloroform solvent mixture). The eluate was concentrated, and the residue was recrystallized from isopropanol/hexane, to thereby yield Compound 15 (0.55 g, 33%).

Example 16

1-[5-O-(tert-Butyldimethylsilyl)-3-C-ethynyl-β-D-ribofuranosyl]-4-N-(tert-butoxycarbonyl)cytosine (Compound 16)

Under ice-cooling, Compound 1 (1.65 g, 4.3 mmol) and di-tert-butyl dicarbonate (1.4 g, 6.5 mmol) were added to tetrahydrofuran (20 mL), and the mixture was stirred for one day at 50° C.
The reaction mixture was concentrated, and the residue was purified through silica gel chromatography (4% methanol/chloroform solvent mixture). The eluate was concentrated, and the residue was recrystallized from hexane, to thereby yield Compound 16 (0.52 g, 26%).

Example 17

1-[5-O-(tert-Butyldimethylsilyl)-3-C-ethynyl-β-D-ribofuranosyl]-4-N-(N,N-dimethylglycyl)cytosine (Compound 17)

Compound 1 (1.9 g, 5 mmol), N,N-dimethylglycine (1.0 g, 10 mmol), N,N-dimethylaminopyridine (0.1 g, 0.8 mmol), and 1-ethyl-3-(3-dimethylaminopropyl)carbodiimide hydrochloride (1.9 g, 10 mmol) were added to DMF (20 mL) under ice-cooling, and the mixture was stirred for one day at 40° C. The reaction mixture was concentrated, and ethyl acetate was added to the residue. The organic layer was washed with saturated aqueous sodium hydrogen carbonate (50 mL) and saturated brine (50 mL), and then dried over magnesium sulfate. Magnesium sulfate was removed through filtration, and the filtrate was concentrated. The residue was purified through silica gel chromatography (4% methanol/chloroform solvent mixture). The eluate was concentrated, and the residue was recrystallized from hexane, to thereby yield Compound 17 (0.46 g, 20%).

Example 18

1-[5-O-(Triisopropylsilyl)-3-C-ethynyl-β-ribofuranosyl]-4-N-(N,N-dimethylglycyl)cytosine (Compound 18)

The procedure of Example 17 was repeated, except that Compound 3 was employed instead of Compound 1 employed in Example 17, whereby Compound 18 was synthesized (yield: 47%).

Structure and physical properties of the compounds obtained in Examples described above are shown in Tables 1 to 5.

TABLE 1

| Ex. | Structure | Instrumental analysis data |
|---|---|---|
| 1 | 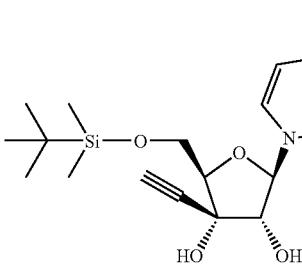 | Properties: colorless powder (ethyl acetate); m.p.: 251 to 256° C. (decomposition); $^1$H-NMR (DMSO-$d_6$) δ 7.80 (1H, d, J = 7.6 Hz), 7.19 (2H, s, disappeared by $D_2O$), 5.93 (1H, d, J = 7.1 Hz), 5.87 (1H, s, disappeared by $D_2O$), 5.75 (1H, d, J = 6.8 Hz, disappeared by $D_2O$), 5.70 (1H, d, J = 7.6 Hz), 4.03 1H, dd, J = 6.8 Hz, 7.1 Hz), 3.77-3.93 (3H, m), 3.55 (1H, s), 0.89 (9H, s), 0.09 (3H, s), 0.08 (3H,s) |

TABLE 1-continued

| Ex. | Structure | Instrumental analysis data |
|---|---|---|
| 2 | (structure) | Properties: colorless powder (ethyl acetate); m.p.: 202 to 204° C.; $^1$H-NMR (DMSO-$d_6$) δ 7.84 (1H, d, J = 7.3 Hz), 7.22 (2H, s, disappeared by $D_2O$), 5.94 (1H, d, J = 7.0 Hz). 5.87 (1H, s, disappeared by $D_2O$), 5.75 (1H, d, J = 6.8 Hz, disappeared by $D_2O$), 5.73 (1H, d, J = 7.3 Hz), 4.07 (1H, dd, J = 6.8 Hz, 7.3 Hz), 3.75-3.95 (3H, m), 3.55 (1H, s), 0.90-1.00 (9H, m), 0.55-0.68 (6H, m) |

TABLE 2

| Ex. | Structure | Instrumental analysis data |
|---|---|---|
| 3 | (structure) | Properties: colorless powder (methanol/ethyl acetate); m.p.: >219° C. (decomposition); $^1$H-NMR (DMSO-$d_6$) δ 7.72 (1H, d, J = 7.6 Hz), 7.12 (2H, br s, disappeared by $D_2O$), 5.90 (1H, d, J = 7.2 Hz), 5.87 (1H, s, disappeared by $D_2O$), 5.79 (1H, d, J = 6.6 Hz, disappeared by $D_2O$), 5.71 (1H, d, J = 7.6 Hz), 4.03 (1H, dd, J = 6.6 Hz, 7.2 Hz), 3.86-3.98 (3H, m), 3.54 (1H, s), 0.90-1.18 (21H, m) |
| 4 | (structure) | Properties: colorless powder (ethyl acetate); m.p.: 175 to 177° C. (decomposition) $^1$H-NMR (DMSO-$d_6$) δ 7.81 (1H, d, J = 7.6 Hz), 7.18 (2H, br s, disappeared by $D_2O$), 5.91 (1H, d, J = 6.8 Hz), 5.86 (1H, s, disappeared by $D_2O$), 5.72 (1H, d, J = 6.8 Hz, disappeared by $D_2O$), 5.70 (1H, d, J = 7.6 Hz), 4.03 (1H, t, J = 6.8 Hz), 3.65-3.95 (3H, m), 3.53 (1H, s), 1.15-1.35 (12H, m), 0.84 (3H, t, J = 6.6 Hz), 0.50-0.65 (2H, m), 0.08 (6H, s) |
| 5 | (structure) | Properties: colorless powder (ethyl acetate); m.p.: 171 to 173° C.; $^1$H-NMR (DMSO-$d_6$) δ 7.72 (1H, d, J = 7.6 Hz), 7.38-7.60 (5H, m), 7.19 (2H, br s, disappeared by $D_2O$), 5.91 (1H, d, J = 6.8 Hz), 5.88 (1H, s, disappeared by $D_2O$), 5.76 (1H, d, J = 6.8 Hz, disappeared by $D_2O$), 5.58 (1H, d, J = 7.6 Hz), 4.05 (1H, t, J = 6.8 Hz), 3.75-3.90 (3H, m), 3.54 (1H, s), 0.39 (3H, s), 0.37 (3H, s) |

TABLE 2-continued

| Ex. | Structure | Instrumental analysis data |
| --- | --- | --- |
| 6 | 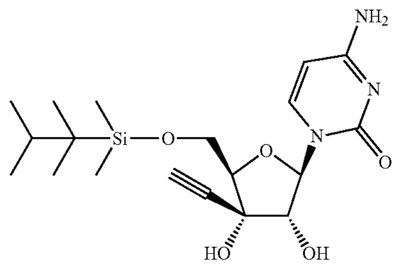 | Properties: colorless powder (ethyl acetate/n-hexane); m.p.: >197° C. (decomposition); ¹H-NMR (DMSO-$d_6$) δ 7.74 (1H, d, J = 7.6 Hz), 7.19 (2H, br s, disappeared by $D_2O$), 5.90 (1H, d, J = 6.8 Hz), 5.86 (1H, s, disappeared by $D_2O$), 5.75 (1H, d, J = 6.8 Hz, disappeared by $D_2O$), 5.71 (1H, d, J = 7.6 Hz), 4.01 (1H, t, J = 6.8 Hz), 3.75-3.90 (3H, m), 3.55 (1H, s), 1.52-1.65 (1H, m), 0.82-0.87 (12H, m), 0.12 (3H, s), 0.11 (3H, s) |

TABLE 3

| Ex. | Structure | Instrumental analysis data |
| --- | --- | --- |
| 7 | 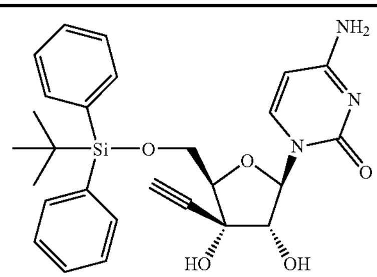 | Properties: colorless powder ($H_2O$); m.p.: 210 to 213° C. ¹H-NMR (DMSO-$d_6$) δ 7.35-7.70 (11H, m), 7.15 (2H, br s, disappeared by $D_2O$), 5.93 (1H, d, J = 6.8 Hz), 5.92 (1H, s, disappeared by $D_2O$), 5.87 (1H, d, J = 6.8 Hz, disappeared by $D_2O$), 5.37 (1H, d, J = 7.6 Hz), 4.12 (1H, t, J = 6.8 Hz), 3.80-4.15 (3H, m), 3.60 (1H, s), 1.02 (9H, s) |
| 8 | 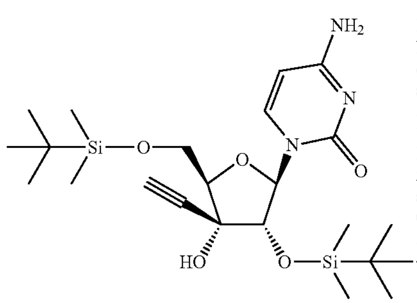 | Properties: white solid; ¹H-NMR (DMSO-$d_6$) δ 7.85 (1H, d, J = 7.3 Hz), 7.20 (2H, br s), 6.06 (1H, d, J = 7.3 Hz), 5.76 (1H, s), 5.73 (1H, d, J = 7.3 Hz), 4.17 (1H, d, J = 7.6 Hz), 3.97 (1H, s), 3.90 (1H, m), 3.80 (1H, m), 3.64 (1H, s), 0.92 (9H, s), 0.80 (9H, s), 0.12, 0.11, 0.01, −0.12 (each 3H, each s); FAB-LRMS m/z 497 (MH⁺). |
| 9 | 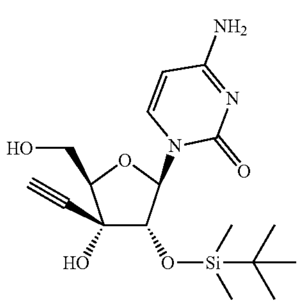 | Properties: white solid; ¹H-NMR (DMSO-$d_6$) δ 7.86 (1H, d, J = 7.3 Hz), 7.18, 7.14 (each 1H, each br s), 5.87 (1H, d, J = 6.9 Hz), 5.74 (1H, d, J = 7.3 Hz), 5.65 (1H, s), 5.09 (1H, t, J = 4.6 Hz), 4.32 (1H, d, J = 6.9 Hz), 3.89-3.91 (1H, m), 3.61-3.88 (2H, m), 3.56 (1H, s), 0.80 (9H, s), 0.03 (3H, s), −0.89 (3H, s); FAB-LRMS m/z 382 (MH⁺); Anal. Calcd for $C_{17}H_{27}N_3O_5Si \cdot 0.7\ H_2O$: C, 51.81; H, 7.26; N, 10.66. Found: C, 52.06; H, 7.09; N, 10.65. |

TABLE 3-continued

| Ex. | Structure | Instrumental analysis data |
|---|---|---|
| 10 | 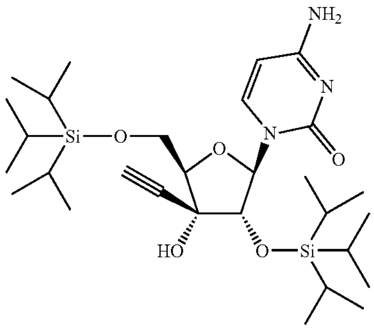 | Properties: colorless foam; $^1$H-NMR (DMSO-$d_6$) δ 7.71 (1H, d, J = 7.3 Hz), 7.18 (2H, br s), 5.96 (1H, d, J = 6.1 Hz), 5.74 (1H, s), 5.71 (1H, d, J = 7.3 Hz), 4.30 (1H, d, J = 6.3 Hz), 3.94 (3H, m), 3.62 (1H, s), 2.49 (9H, s), 1.06-0.95 (42H, m); FAB-LRMS m/z 580 (MH$^+$); Anal. Calcd for $C_{29}H_{53}N_2O_5Si$: C, 60.06; H, 9.21; N, 7.25. Found: C, 59.08; H, 9.23; N, 7.15. |
| 11 | 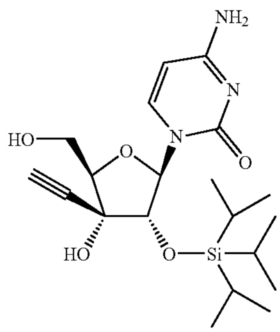 | Properties: white solid; $^1$H-NMR (DMSO-$d_6$) δ 7.84 (1H, d, J = 7.3 Hz), 7.18, 7.14 (each 1H, each br s), 5.88 (1H, d, J = 6.3 Hz), 5.73 (1H, d, J = 7.3 Hz), 5.64 (1H, s), 5.10 (1H, t, J = 4.6 Hz), 4.50-4.53 (1H, m), 3.87-3.89 (1H, m), 3.61-3.73 (2H, m), 3.56 (1H, s), 0.95-1.05 (21H, m) |

TABLE 4

| Ex. | Structure | Instrumental analysis data |
|---|---|---|
| 12 | 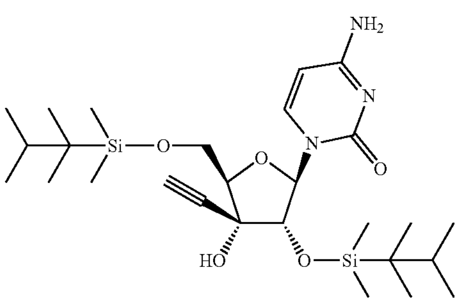 | Properties: colorless foam; m.p.: 106 to 108° C. $^1$H-NMR (DMSO-$d_6$) δ 7.78 (1H, d, J = 7.3 Hz), 7.19 (2H, br s), 6.03 (1H, d, J = 7.3 Hz), 5.73 (1H, d, J = 7.3 Hz), 5.65 (1H, s), 4.13 (2H, d, J = 7.6 Hz), 3.95 (1H, s), 3.90 (1H, dd, J = 2.3 Hz, J = 11.5 Hz), 3.81 (1H, dd, J = 2.3 Hz, J = 11.5 Hz), 3.63 (1H, s), 1.58 (2H, m), 0.80 (24H, m), 0.15, 0.14, 0.08, −0.10 (each 3H, each s); FAB-LRMS m/z 552 (MH$^+$); Anal. Calcd for $C_{27}H_{49}N_3O_5Si_2$: C, 58.76; H, 8.95; N, 7.61. Found: C, 58.48; H, 8.93; N, 7.85. |
| 13 | 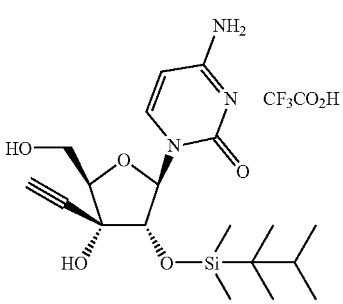 | Properties: white solid; m.p.: 182° C. $^1$H-NMR (DMSO-$d_6$) δ 9.22 (1H, br s), 8.44 (1H, br s), 8.23 (1H, d, J = 7.9 Hz), 6.09 (1H, d, J = 7.9 Hz), 5.85 (1H, d, J = 6.3 Hz), 4.32 (1H, d, J = 6.3 Hz), 3.89 (1H, m), 3.74 (2H, m), 3.66 (1H, s), 1.55 (1H, m), 0.79 (12H, m), 0.14, −0.01 (each 3H, each s); FAB-LRMS (negative) m/z 522 (M − H)$^-$; Anal. Calcd for $C_{21}H_{32}F_3N_3O_7Si \cdot 0.7 H_2O$: C, 47.04; H, 6.28; N, 7.84. Found: C, 47.59; H, 6.27; N, 8.11. |

TABLE 4-continued

| Ex. | Structure | Instrumental analysis data |
|---|---|---|
| 14 | 4-amino-1-[(2R,3R,4R,5R)-3-(tert-butyldimethylsilyloxy)-4-hydroxy-5-(hydroxymethyl)-4-ethynyltetrahydrofuran-2-yl]pyrimidin-2(1H)-one (structure with NH$_2$-cytosine base, 5'-OH, 3'-OH, 4'-ethynyl, 2'-OTBS) | Properties: white solid; m.p.: 218° C. $^1$H-NMR(DMSO-d$_6$) δ 7.85 (1H, d, J = 7.3 Hz), 7.17 (2H, br d, J = 11.9 Hz), 5.86 (1H, d, J = 6.9 Hz), 5.74 (1H, d, J = 7.3 Hz), 5.57 (1H, s), 5.10 (1H, m), 4.33 (1H, d, J = 6.9 Hz), 3.89 (1H, m), 3.67 (2H, m), 3.57 (1H, s), 1.53 (1H, m), 0.78 (12H, m), 0.10, −0.06 (each 3H, each s); FAB-LRMS m/z 410 (MH$^+$); Anal. Calcd for C$_{19}$H$_{31}$N$_3$O$_3$Si·0.6 H$_2$O: C, 54.29; H, 7.72; N, 10.00. Found: C, 54.18; H, 7.69; N, 9.97. |
| 15 | N-heptanoyl cytidine analog with 5'-OTBS, 4'-ethynyl, 3'-OH, 2'-OH (structure shown) | Properties: colorless powder (isopropanol/hexane); m.p.: 134 to 137° C.; $^1$H-NMR (DMSO-d$_6$) δ 10.90 (1H, s, disappeared by D$_2$O), 8.24 (1H, d, J = 7.6 Hz), 7.24 (1H, d, J = 7.6 Hz), 6.00 (1H, s, disappeared by D$_2$O), 5.94 (1H, d, J = 6.3 Hz), 5.83 (1H, d, J = 6.3 Hz, disappeared by D$_2$O), 4.09 (1H, t, J = 6.3 Hz), 3.82-4.04 (3H, m), 3.58 (1H, s), 2.38 (2H, t, J = 7.3 Hz), 1.49-1.54 (2H, m), 1.17-1.34 (6H, m), 0.79-0.93 (12H, m), 0.11 (3H, s), 0.09 (3H, s) |

TABLE 5

| Ex. | Structure | Instrumental analysis data |
|---|---|---|
| 16 | N-Boc cytidine analog with 5'-OTBS, 4'-ethynyl, 3'-OH, 2'-OH (structure shown) | Properties: colorless powder (hexane); m.p.: 103 to 110° C.; $^1$H-NMR (DMSO-d$_6$) δ 10.40 (1H, s, disappeared by D$_2$O), 8.18 (1H, d, J = 7.8 Hz), 7.00 (1H, d, J = 7.3 Hz), 5.98 (1H, s, disappeared by D$_2$O), 5.93 (1H, d, J = 6.4 Hz, disappeared by D$_2$O), 5.80 (1H, d, J = 7.8 Hz), 4.08 (1H, dd, J = 6.4 Hz, 7.3 Hz), 3.8-4.00 (3H, m), 3.56 (1H, s), 1.44 (9H, s), 0.89 (9H, s), 0.10 (3H, s), 0.09 (3H, s) |
| 17 | N-(dimethylamino)acetyl cytidine analog with 5'-OTBS, 4'-ethynyl, 3'-OH, 2'-OH (structure shown) | Properties: colorless powder (hexane); m.p.: 180 to 185° C.; $^1$H-NMR (DMSO-d$_6$) δ 10.38 (1H, s, disappeared by D$_2$O), 8.27 (1H, d, J = 7.3 Hz), 7.22 (1H, d, J = 7.3 Hz), 5.87-6.05 (3H, m, 2H disappeared by D$_2$O), 3.82-4.06 (4H, m), 3.57 (1H, s), 3.14 (2H, s), 0.89 (9H, s), 0.10 (3H, s), 0.09 (3H, s) |

TABLE 5-continued

| Ex. | Structure | Instrumental analysis data |
|---|---|---|
| 18 | (structure shown) | Properties: colorless powder (diisopropyl ether); m.p.: 146 to 148° C.; $^1$H-NMR (DMSO-$d_6$) δ; 10.39 (1H, s, disappeared by $D_2O$), 8.20 (1H, d, J = 7.6 Hz), 7.23 (1H, d, J = 7.6 Hz), 6.03 (1H, s, disappeared by $D_2O$), 5.99 (1H, d, J = 5.9 Hz), 5.89 (1H, d, J = 5.4 Hz), 3.94-4.14 (4H, m), 3.85 (1H, s), 3.16 (2H, s), 2.27 (6H, s), 0.95-1.20 (21H, m) |

Pharmacological Test Example 1
Antitumor Effect of the Compound of the Present Invention When Perorally Administered to Donryu Rat Subcutaneous Tumor Implantation System Cells of a Yoshida Sarcoma cell line (rat ascites tumor) intraperitoneally subcultured in Donryu rats (Charles River Laboratories Japan, Inc.) were implanted subcutaneously to 5-week-old Donryu rats in the back thereof at $2 \times 10^4$ cells/0.2 mL. Four days after implantation, the body weight of each rat was measured, and the rats were grouped so that the average body weight was nearly equal between the groups (7 rats per group).

Each of the ECyd derivatives was dissolved or suspended in 0.5% hydroxypropylmethylcellulose solution, and the resultant solution or suspension was perorally administered to each rat every day from the day of grouping once a day for seven days at a dose of 12 μmol/kg/day. The ECyd derivative was evaluated three times. As a control in each test, ECyd was used in an equimolar amount as the ECyd derivative.

Seven days after the day of grouping, the tumor weight of the rat in the pharmaceutical agent administration group was measured. The tumor weight of the rat to which no pharmaceutical agent had been administered (non-treatment group) was also measured. The average tumor weight of each of the pharmaceutical agent administration group and the non-treatment group was calculated. Tumor growth inhibition rate (IR) was determined through use of the following equation, whereby antitumor effect was evaluated.

$$IR(\%) = [1-(TWtest)/(TWcont)] \times 100 \quad \text{(Equation 1)}$$

[wherein TWtest and TWcont represent the average tumor weight of the pharmaceutical agent administration group and the non-treatment group, respectively].

The test results are shown in Table 6.

TABLE 6

| Compound No. | IR (%) |
|---|---|
| 1 | 94.6 |
| 3 | 93.4 |
| 9 | 99.6 |
| 11 | 88.3 |
| 12 | 91.5 |
| 13 | 99.8 |
| 14 | 99.8 |
| ECyd | 46.6 |

As shown in Table 6, when orally administered, the compound of the present invention was found to exhibit excellent antitumor effect as compared with ECyd.

Separately, the compound of the present invention was perorally administered to Donryu male rats, and serum ECyd level was measured. The compound of the present invention was found to exhibit very high concentration in blood as compared with ECyd. For example, Compounds 1, 3, 4, 9, 11, 12, 14, 15, 17, and 18 exhibited particularly high concentration in blood.

Preparation Example 1 Tablets

TABLE 7

| Compound 1 | 50 mg |
|---|---|
| Corn starch | 50 mg |
| Microcrystalline cellulose | 50 mg |
| Hydroxypropyl cellulose | 15 mg |
| Lactose | 47 mg |
| Talc | 2 mg |
| Magnesium stearate | 2 mg |
| Ethyl cellulose | 30 mg |
| Unsaturated glyceride | 2 mg |
| Titanium dioxide | 2 mg |

Tablets, each weighing 250 mg and having the above composition, were prepared through a routine method.

Preparation Example 2 Granules

TABLE 8

| Compound 9 | 300 mg |
|---|---|
| Lactose | 540 mg |
| Corn starch | 100 mg |
| Hydroxypropyl cellulose | 50 mg |
| Talc | 10 mg |

Granules (1,000 mg/sachet), having the above composition, were prepared through a routine method.

Preparation Example 3 Capsules

TABLE 9

| Compound 11 | 100 mg |
|---|---|
| Lactose | 30 mg |
| Corn starch | 50 mg |
| Microcrystalline cellulose | 10 mg |
| Magnesium stearate | 3 mg |

Capsules, each weighing 193 mg and having the above composition, were prepared through a routine method.

Preparation Example 4 Injection

TABLE 10

| Compound 2 | 100 mg |
|---|---|
| Sodium chloride | 3.5 mg |
| Distilled water for injection | Appropriate amount (2 mL/ample) |

Injection liquid having the above composition was prepared through a routine method.

Preparation Example 5 Syrup

TABLE 11

| Compound 3 | 200 mg |
|---|---|
| Purified sucrose | 60 g |
| Ethyl p-hydroxybenzoate | 5 mg |
| Butyl p-hydroxybenzoate | 5 mg |
| Flavor | Appropriate amount |
| Coloring agent | Appropriate amount |
| Purified water | Appropriate amount |

Syrup having the above composition was prepared through a routine method.

Preparation Example 6 Suppositories

TABLE 12

| Compound 14 | 300 mg |
|---|---|
| Witepsol W-35 (registered trademark, a mixture of mono-, di-, and tri-glyceride of saturated fatty acids (lauric to stearic), product of Dynamite Novel) | 1,400 mg |

Suppositories having the above composition were prepared through a routine method.

INDUSTRIAL APPLICABILITY

The 3'-ethynylcytidine derivative or a salt thereof of the present invention is a useful anti-tumor drug which exhibits excellent anti-tumor activity and excellent oral absorption. Therefore, problems involved in intravenous administration of a drug and imposed on patients; i.e., mental and physical pains and excessively high medical cost of outpatient treatment, can be solved, whereby remarkable improvement of the quality of life (QOL) of patients is expected.

The invention claimed is:

1. A 3'-ethynylcytidine derivative represented by formula (1):

[F1]

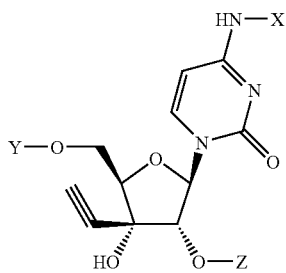

(1)

wherein X represents a hydrogen atom, an alkylcarbonyl group of which alkyl moiety is a substituted or unsubstituted C1-C6 linear or branched alkyl group, or an alkoxycarbonyl group of which alkoxy moiety is a substituted or unsubstituted C1-C6 linear or branched alkoxy group; one of Y and Z represents a hydrogen atom or a group $(R^1)(R^2)(R^3)Si$- and the other represents a group $(R^4)(R^5)(R^6)Si$—; and $R^1$, $R^2$, $R^3$, $R^4$, $R^5$, and $R^6$, which may be identical to or different from one another, each represent a substituted or unsubstituted C1-C10 linear or branched alkyl group, a substituted or unsubstituted C3-C6 cycloalkyl group, or a substituted or unsubstituted C6-C14 aryl group, or a salt thereof.

2. A 3'-ethynylcytidine derivative or a salt thereof as described in claim 1, wherein, in formula (1), X is a hydrogen atom, an alkylcarbonyl group of which alkyl moiety is a C1-C6 linear or branched alkyl group which is optionally substituted with an amino group mono- or di-substituted by a C1-C6 linear or branched alkyl group, or an alkoxycarbonyl group of which alkoxy moiety is a C1-C6 linear or branched alkoxy group; one of Y and Z is a hydrogen atom or a group $(R^1)(R^2)(R^3)Si$— and the other is a group $(R^4)(R^5)(R^6)Si$—; and $R^1$, $R^2$, $R^3$, $R^4$, $R^5$, and $R^6$, which may be identical to or different from one another, each are a C1-C10 linear or branched alkyl group, a C3-C6 cycloalkyl group, or a C6-C14 aryl group.

3. A 3'-ethynylcytidine derivative or a salt thereof as described in claim 1, wherein, in formula (1), X is a hydrogen atom, an alkylcarbonyl group of which alkyl moiety is a C1-C6 linear or branched alkyl group optionally substituted with a dimethylamino group, or an alkoxycarbonyl group of which alkoxy moiety is a C1-C6 linear or branched alkoxy group; one of Y and Z is a hydrogen atom or a group $(R^1)(R^2)(R^3)Si$— and the other is a group $(R^4)(R^5)(R^6)Si$—; and $R^1$, $R^2$, $R^3$, $R^4$, $R^5$, $R^6$, which may be identical to or different from one another, each are a C1-C10 linear or branched alkyl group, a C3-C6 cycloalkyl group, or a C6-C14 aryl group.

4. A 3'-ethynylcytidine derivative or a salt thereof as described in claim 1, wherein, in formula (1), X is a hydrogen atom; one of Y and Z is a hydrogen atom or a group $(R^1)(R^2)(R^3)Si$— and the other is a group $(R^4)(R^5)(R^6)Si$—; and $R^1$, $R^2$, $R^3$, $R^4$, $R^5$, and $R^6$, which may be identical to or different from one another, each are a C1-C10 linear or branched alkyl group, a C3-C6 cycloalkyl group, or a C6-C14 aryl group.

5. A 3'-ethynylcytidine derivative or a salt thereof as described in claim 1, wherein, in formula (1), X is a hydrogen atom; one of Y and Z is a hydrogen atom or a group $(R^1)(R^2)(R^3)Si$— and the other is a group $(R^4)(R^5)(R^6)Si$—; and $R^1$, $R^2$, $R^3$, $R^4$, $R^5$, and $R^6$, which may be identical to or different from one another, each are a C1-C8 linear or branched alkyl group or a phenyl group.

6. A 3'-ethynylcytidine derivative or a salt thereof as described in claim 1, wherein, in formula (1), X is a hydrogen atom; one of Y and Z is a hydrogen atom and the other is a group $(R^4)(R^5)(R^6)Si$—; and $R^4$, $R^5$, and $R^6$, which may be identical to or different from one another, each are a C1-C8 linear or branched alkyl group or a phenyl group.

7. A 3'-ethynylcytidine derivative or a salt thereof as described in claim 1, wherein, in formula (1), X is a hydrogen atom; one of Y and Z is a hydrogen atom and the other is a tert-butyldimethylsilyl group, a triethylsilyl group, a triisopropylsilyl group, a dimethyl-n-octylsilyl group, a dimethylphenylsilyl group, a dimethylthexylsilyl group, or a tert-butyldiphenylsilyl group.

8. At least one 3'-ethynylcytidine derivative or salt thereof selected from the group consisting of:
(1) 1-[5-O-(tert-butyldimethylsilyl)-3-C-ethynyl-β-D-ribofuranosyl]cytosine, (2) 1-[5-O-triethylsilyl-3-C-ethynyl-β-D-ribofuranosyl]cytosine,
(3) 1-[5-O-triisopropylsilyl-3-C-ethynyl-β-D-ribofuranosyl]cytosine,
(4) 1-[5-O-(dimethyl-n-octylsilyl)-3-C-ethynyl-β-D-ribofuranosyl]cytosine,
(5) 1-[5-O-dimethylphenylsilyl-3-C-ethynyl-β-D-ribofuranosyl]cytosine,
(6) 1-[5-O-dimethylthexylsilyl-3-C-ethynyl-β-D-ribofuranosyl]cytosine,
(7) 1-[5-O-(tert-butyldiphenylsilyl)-3-C-ethynyl-β-D-ribofuranosyl]cytosine,
(8) 1-[2,5-bis-O-(tert-butyldimethylsilyl)-3-C-ethynyl-1-β-D-ribofuranosyl]cytosine,
(9) 1-[2-O-(tert-butyldimethylsilyl)-3-C-ethynyl-1-β-D-ribofuranosyl]cytosine,
(10) 1-(2,5-bis-O-triisopropylsilyl-3-C-ethynyl-1-β-D-ribofuranosyl)cytosine,
(11) 1-(2-O-triisopropylsilyl-3-C-ethynyl-1-β-D-ribofuranosyl)cytosine,
(12) 1-(2,5-bis-O-dimethylthexylsilyl-3-C-ethynyl-1-β-D-ribofuranosyl)cytosine,
(13) 1-(2-O-dimethylthexylsilyl-3-C-ethynyl-1-β-D-ribofuranosyl)cytosine,
(14) 1-[5-O-(tert-butyldimethylsilyl)-3-C-ethynyl-β-D-ribofuranosyl]-4-N-heptanoylcytosine,
(15) 1-[5-O-(tert-butyldimethylsilyl)-3-C-ethynyl-β-D-ribofuranosyl]-4-N-(tert-butoxycarbonyl)cytosine,
(16) 1-[5-O-(tert-butyldimethylsilyl)-3-C-ethynyl-β-D-ribofuranosyl]-4-N-(N,N-dimethylglycyl)cytosine, and
(17) 1-[5-O-(triisopropylsilyl)-3-C-ethynyl-β-D-ribofuranosyl]-4-N-(N,N-dimethylglycyl)cytosine.

9. A pharmaceutical composition comprising a 3'-ethynylcytidine derivative or a salt thereof as recited in claim 1 and a pharmaceutical carrier.

10. An anti-tumor drug containing a 3'-ethynylcytidine derivative or a salt thereof as recited in claim 1 and a pharmaceutical carrier.

11. An oral anti-tumor drug containing a 3'-ethynylcytidine derivative or a salt thereof as recited in claim 1 and a pharmaceutical carrier.

12. A method for treatment of tumor, wherein the method comprises administering a 3'-ethynylcytidine derivative or a salt thereof as recited in claim 1 in an effective amount to a subject in need thereof.

13. A method for treatment of tumor as described in claim 12, wherein the administering is oral administration.

14. A pharmaceutical composition comprising at least one 3'-ethynylcytidine derivative or a salt thereof as recited in claim 8 and a pharmaceutical carrier.

15. A method for treatment of tumor, wherein the method comprises administering at least one 3'-ethynylcytidine derivative or a salt thereof as recited in claim 8 in an effective amount to a subject in need thereof.

* * * * *